(12) United States Patent
Muni et al.

(10) Patent No.: US 9,913,964 B2
(45) Date of Patent: Mar. 13, 2018

(54) SYSTEM AND METHOD FOR DILATING AN AIRWAY STENOSIS

(75) Inventors: Ketan P. Muni, San Jose, CA (US); Hung V. Ha, San Jose, CA (US); Chi Nguyen, Belmont, CA (US); Randy S. Chan, San Jose, CA (US); John Y. Chang, Mountain View, CA (US)

(73) Assignee: Acclarnet, Inc., Irvine, CA (US)

( * ) Notice: Subject to any disclaimer, the term of this patent is extended or adjusted under 35 U.S.C. 154(b) by 1435 days.

(21) Appl. No.: 12/566,556

(22) Filed: Sep. 24, 2009

(65) Prior Publication Data

US 2010/0168511 A1 Jul. 1, 2010

Related U.S. Application Data

(60) Provisional application No. 61/141,146, filed on Dec. 29, 2008.

(51) Int. Cl.
*A61M 29/00* (2006.01)
*A61M 25/01* (2006.01)
(Continued)

(52) U.S. Cl.
CPC .... *A61M 25/0152* (2013.01); *A61M 25/0102* (2013.01); *A61M 25/10* (2013.01); *A61M 25/1027* (2013.01); *A61M 29/02* (2013.01); *A61B 2090/306* (2016.02); *A61M 25/0041* (2013.01); *A61M 2025/1031* (2013.01); *A61M 2025/1088* (2013.01)

(58) Field of Classification Search
CPC .............. A61M 25/0152; A61M 25/10; A61M 25/0102; A61M 25/1006
USPC .................. 606/191, 192, 199, 194; 604/528
See application file for complete search history.

(56) References Cited

U.S. PATENT DOCUMENTS 5,352,199 A * 10/1994 Tower .................... A61M 29/02
604/103.07
5,700,243 A * 12/1997 Narciso, Jr. .............. 604/102.01
(Continued)

FOREIGN PATENT DOCUMENTS

EP 0335022 10/1989
JP 2004-305250 11/2004
(Continued)

OTHER PUBLICATIONS

Mayse, M., J. Greenheck, M. Friedman & K. Kovitz. (2004). Successful Bronchoscopic Balloon Dilation of Nonmalignant Tracheobronchial Obstruction Without Fluoroscopy. Chest, 126: 634-637.*

(Continued)

*Primary Examiner* — Katherine Rodjom
(74) *Attorney, Agent, or Firm* — Frost Brown Todd LLC

(57) ABSTRACT

A method for dilating a stenotic region in an airway of a patient may include advancing a balloon catheter through the airway of the patient to position an inflatable balloon of the catheter within at least a portion of the stenotic region, maintaining a position of the catheter relative to the patient, and inflating the balloon of the catheter to dilate the stenotic region of the airway. A system for dilating a stenotic region in an airway of a patient may include a catheter shaft having an overall length of less than 70 cm, an inflatable balloon disposed along a distal portion of the catheter shaft, and a stylet.

18 Claims, 9 Drawing Sheets

(51) Int. Cl.
*A61M 25/10* (2013.01)
*A61M 29/02* (2006.01)
*A61M 25/00* (2006.01)
*A61B 90/30* (2016.01)

(56) References Cited

U.S. PATENT DOCUMENTS

| | | | |
|---|---|---|---|
| 5,769,814 A * | 6/1998 | Wijay | A61M 25/003 604/103.1 |
| 7,273,487 B1 * | 9/2007 | Duchamp | A61M 25/0045 604/525 |
| 7,993,350 B2 | 8/2011 | Ventura et al. | |
| 2004/0073250 A1 * | 4/2004 | Pederson, Jr. | A61F 2/958 606/192 |
| 2005/0240147 A1 | 10/2005 | Makower et al. | |
| 2006/0004323 A1 * | 1/2006 | Chang et al. | 604/28 |
| 2006/0063973 A1 * | 3/2006 | Makower et al. | 600/114 |
| 2007/0282367 A1 * | 12/2007 | Jeffrey et al. | 606/194 |
| 2008/0097465 A1 * | 4/2008 | Rollins et al. | 606/108 |
| 2008/0269684 A1 * | 10/2008 | Anderson et al. | 604/170.02 |
| 2009/0018525 A1 * | 1/2009 | Waite | A61M 25/005 604/508 |
| 2009/0036834 A1 * | 2/2009 | Voeller et al. | 604/164.13 |
| 2010/0063534 A1 * | 3/2010 | Kugler et al. | 606/200 |
| 2010/0125244 A1 * | 5/2010 | McAndrew | 604/98.01 |
| 2010/0217372 A1 * | 8/2010 | Lentz | 623/1.11 |

FOREIGN PATENT DOCUMENTS

| | | |
|---|---|---|
| JP | 2006-516451 | 7/2006 |
| WO | WO2006135853 | 12/2006 |
| WO | WO2008033179 | 3/2008 |

OTHER PUBLICATIONS

Australian Office Action, Patent Examination Report No. 1 dated Oct. 14, 2014 re Application No. 2009333013.
Chinese Office Action dated Jan. 21, 2013 re Application No. CN 20090153746.
Chinese Office Action dated Oct. 8, 2013 re Application No. CN 200980153746.
Chinese Office Action dated Apr. 28, 2014 re Application No. CN 200980153746.
Chinese Office Action dated Oct. 31, 2014 re Application No. CN 200980153746.
Chinese Office Action dated May 20, 2015 re Application No. CN 200980153746.
Chinese First Search Report dated Jan. 10, 2013 re Application No. CN 200980153746.
Chinese Supplemental Search Report dated Sep. 22, 2013 re Application No. CN 200980153746.
Chinese Supplemental Search Report dated Apr. 18, 2014 re Application No. CN 200980153746.
Chinese Supplemental Search Report dated Oct. 17, 2014 re Application No. CN 200980153746.
First Notice dated Apr. 29, 2010 re Application No. PCT/US2009/069170.
International Preliminary Report on Patentability dated Jun. 11, 2011 re Application No. PCT/US2009/069170.
Japanese Notice of Reasons for Refusal dated Nov. 29, 2013 re Application No. 2011-543635.
Mexican Office Action dated Oct. 30, 2013 re Application No. MX/A/2011/007038.
Mexican Office Action dated May 15, 2014 re Application No. MX/A/2011/007038.
Mexican Office Action dated Oct. 6, 2014 re Application No. MX/A/2011/007038.
Mexican Office Action dated Nov. 6, 2014 re Application No. MX/A/2011/007038.
Mexican Office Action dated Jun. 22, 2015 re Application No. MX/A/2011/007038.
Russian Office Action dated Jul. 24, 2013 re Application No. 2011131865.
Russian Office Action dated Dec. 19, 2013 re Application No. 2011131865.
Mayse, Martin L., "Successful Bronchoscopic Balloon Dilation of Nonmalignant Tracheobronchial Obstruction Without Fluoroscopy", Aug. 2004; vol. 126, Issue 2; pp. 634-637; CHEST Journal of the American College of Chest Physicians.
Canadian Examination Report dated Jan. 26, 2016 for Application No. 2,748,535, 4 pages.
European Examination Report dated Oct. 29, 2013 for Application No. 09804102.3, 4 pages.
International Search Report and Written Opinion dated Apr. 22, 2010 for Application No. PCT/US2009/069170, 10 pages.
Mexican Office Action dated Apr. 24, 2015 for Application No. MX/A/2011/007038, 4 pages.

* cited by examiner

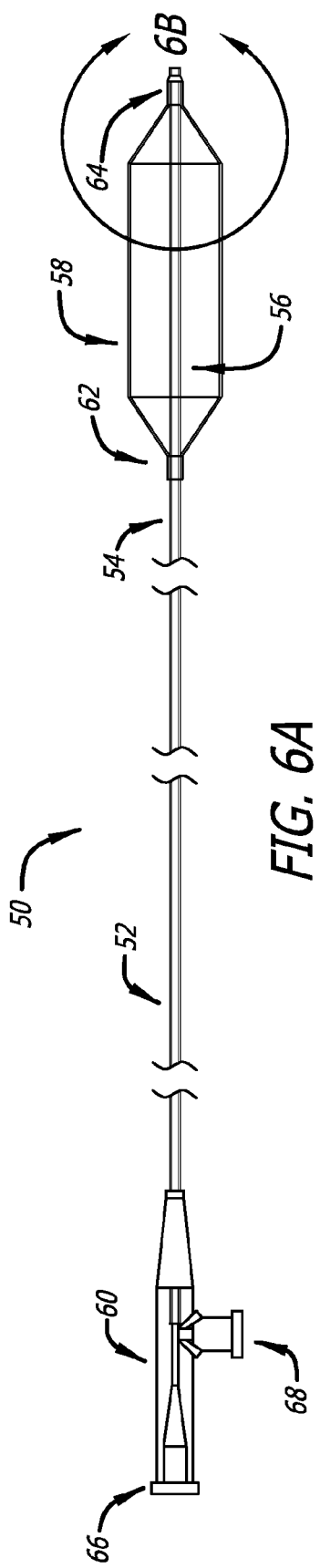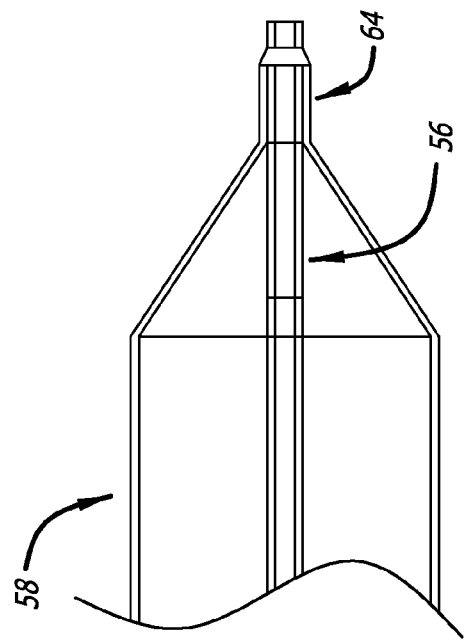
FIG. 6A
FIG. 6B

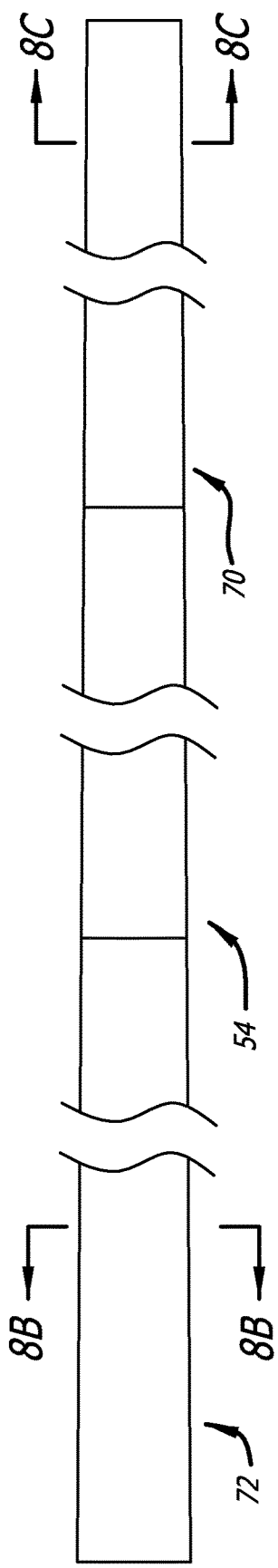
FIG. 8A
FIG. 8B
FIG. 8C

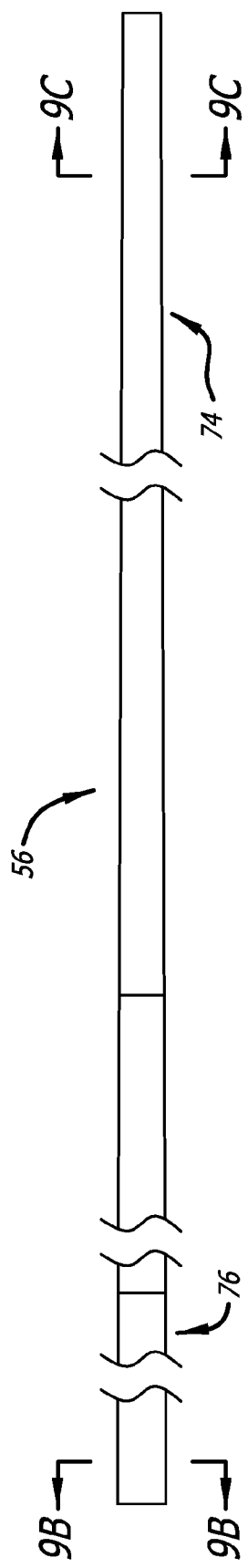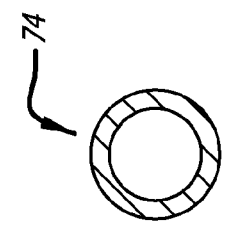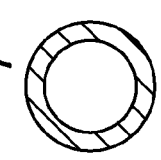

SYSTEM AND METHOD FOR DILATING AN AIRWAY STENOSIS

CROSS-REFERENCES TO RELATED APPLICATIONS

This application claims the benefit of U.S. Provisional Patent Application Ser. No. 61/141,146, filed Dec. 29, 2008, the full disclosure of which is hereby incorporated by reference.

TECHNICAL FIELD

Disclosed herein are a system and method for treating a stenosis in an airway of a patient, and more specifically, a system and method for dilating a stenotic region in an airway of the patient.

BACKGROUND

Airway stenosis (or "airway narrowing") is a medical condition that occurs when some portion of a patient's airway becomes narrowed or constricted, thus making breathing difficult. A stenosis may occur in any part of the airway—i.e., larynx, trachea, bronchi or a combination (laryngotracheal or tracheobronchial stenosis)—in adults or children, and due to any of several different causes. By far the most common airway stenoses (approximately 95%) are acquired, meaning the patient is not born with the condition, and the most common cause of airway stenosis is trauma caused by intubation (a tube placed in the airway for ventilation/breathing assistance in a patient who cannot breathe). Intubation for prolonged periods of time may traumatize the airway, causing scar tissue formation that forms the stenosis. Sometimes the cause of stenosis is unknown, such as in idiopathic subglottic stenosis. Managing airway stenosis is one of the most challenging problems for an ENT (ear, nose and throat) surgeon.

Subglottic stenosis is one form of airway stenosis that occurs in the larynx, below the glottis (the area of the larynx around the vocal cords). The disorder can be either congenital or acquired and can affect both adults and children. Acquired subglottic stenosis is the most common acquired anomaly of the larynx in children and the most common abnormality requiring tracheotomy in children younger than one year. To correct subglottic stenosis, the lumen of the cricoid area is expanded to increase airflow during breathing. Surgical correction of sublottic stenosis has been performed with various techniques over the years.

Therapies for treating airway stenosis range from endoscopic treatments, such as dilation and laser resection, to open procedures, such as laryngotracheal reconstruction. In one technique, a series of rigid dilators of increasing diameter are pushed down the airway, gradually expanding the constriction but also applying unwanted shear forces to the airway. More recently, balloon catheters have been used to perform airway dilation. One of the benefits of balloon dilation over rigid dilation is the application of radial force versus shear force, which reduces the risk of mucosal trauma. Also, depending on the balloon catheter used, a surgeon has greater confidence in the precise amount of pressure needed to dilate the stenotic region of the airway.

Today, most airway dilations using balloon catheters are performed using angioplasty balloon catheters and peripheral balloon catheters, which are designed for dilating narrowed blood vessels. These balloon catheters have several limitations when used for dilating an airway stenosis. First, because these balloons catheters are not specifically designed to be used in the airway, the dimensions of existing balloons may not be optimized for ease of use within pediatric and/or adult airways. Second, current balloon catheters are generally not sized to allow convenient visualization of airway balloon dilation using an endoscope (e.g., laryngoscope or bronchoscope), and in fact in some cases it is not possible to view the airway dilation procedure using an endoscope. Third, balloon catheters used for vascular procedures are generally very long and floppy, which may make them difficult to advance into a constriction in an airway and which may lead to a tendency of the balloons of such catheters to slip or "watermelon seed" out of the constriction when inflated. In general, it can be challenging to position a currently available balloon catheter in a desired location for an airway procedure, dilate the balloon without having it slip out of the narrowed portion of the airway, and visualize the procedure.

Therefore, it would be desirable to have an airway stenosis balloon dilation system that is designed to be used in an airway, rather than in a blood vessel or some other anatomical structure. Ideally, such a system would have dimensions configured for use in an airway, would allow for visualization of at least part of an airway dilation procedure and/or of the system during the procedure, and could be advanced into (and maintained within) an airway constriction more easily than currently available balloon catheters. At least some of these objectives are addressed by the embodiments described in this application.

SUMMARY

Disclosed herein are a system and method for dilating a stenotic region in an airway of a patient. The method generally includes advancing a balloon catheter through the airway of the patient to position an inflatable balloon of the catheter within at least a portion of the stenotic region, maintaining a position of the catheter relative to the patient, and inflating the balloon of the catheter to dilate the stenotic region of the airway. The system generally includes a catheter shaft having an overall length of less than 70 cm, an inflatable balloon disposed along a distal portion of the catheter shaft, and a stylet.

In one aspect, a method for dilating a stenotic region in an airway of a patient may involve: advancing a balloon catheter having a proximal portion, a distal portion more flexible than the proximal portion, and an overall length less than 70 cm through the airway of the patient to position an inflatable balloon of the catheter within at least a portion of the stenotic region, wherein a stylet disposed in the catheter facilitates the advancing; maintaining a position of the catheter relative to the patient to maintain the position of the balloon within the stenotic region by holding the proximal portion of the balloon catheter; and inflating the balloon of the catheter with the stylet in the catheter to dilate the stenotic region of the airway.

In one embodiment, advancing the balloon catheter may involve advancing a distal portion of the stylet into and through the stenotic region, the stylet having a length allowing the distal portion to protrude beyond a distal end of the catheter. Optionally, the method may further involve rotating the stylet within the balloon catheter to steer the distal end of the stylet through the stenotic region. In an alternative embodiment, the method may involve locking the stylet relative to the balloon catheter and rotating the balloon catheter to steer the stylet through the stenotic region.

Some embodiments may optionally further include advancing a scope into a position within the airway of the patient near the stenotic region and visualizing placement of the inflatable balloon within the stenotic region using the scope. Some embodiments may also include viewing at least one shaft marker on a shaft of the balloon catheter using the scope and approximating a location of the inflatable balloon relative to the stenotic region, based on a location of the shaft marker. In one embodiment, the method may involve inserting a bronchoscope into the airway of the patient before the advancing step, and the balloon catheter is advanced through the airway through the bronchoscope.

In some embodiment, before the advancing step, the method may include forming a bend in the stylet, where the bent stylet maintains the balloon catheter in a bent configuration. In one embodiment, the method may involve removing the balloon catheter and stylet from the airway after the advancing step, forming a bend in the stylet, wherein the bent stylet maintains the balloon shaft in a bent configuration, and reintroducing the balloon catheter and stylet into the airway.

In one embodiment, the method may optionally involve removing the stylet from a stylet lumen of the catheter and delivering oxygen through the stylet lumen into the airway. In alternative embodiments, the method may be performed on either pediatric or adult patients.

In another aspect, a system for dilating a stenotic region in an airway of a patient may include: a catheter shaft having a proximal portion, a distal portion, a stylet lumen, an inflation lumen and an overall length of less than 70 cm; an inflatable balloon disposed along the distal portion of the catheter shaft and in fluid communication with the inflation lumen; and a stylet having a proximal portion, a distal portion, and a length sufficient to allow the stylet to extend beyond a distal end of the catheter shaft when the stylet is housed within the stylet lumen, wherein the stylet proximal portion is less flexible than the stylet distal portion and the stylet distal portion is bendable and able to retain a bent configuration when disposed within the stylet lumen.

In some embodiments, the catheter shaft distal portion may be more flexible than the catheter shaft proximal portion. Optionally, the catheter shaft distal portion may have a smaller outer diameter than the catheter shaft proximal portion. In one embodiment, the catheter shaft may include: an inner member forming the stylet lumen; and an outer member disposed over part of the inner member, where the inner member extends beyond a distal end of the outer member, a proximal end of the balloon is attached to the outer member and a distal end of the balloon is attached to the inner member, and a space between the inner member and the outer member forms the inflation lumen of the catheter shaft. One embodiment may further include a hub attached to a proximal end of the outer member, and the hub may include an inflation port in communication with the inflation lumen and a stylet port in communication with the stylet lumen. In one embodiment, the inner member may include a distal segment having a larger outer diameter than the remainder of the inner member, and the balloon may be attached to the inner member at the distal segment. In one embodiment, the balloon may have an outer diameter of at least 12 mm. In one embodiment, an inner diameter of the inner member is no more than about 1.2 mm and an outer diameter of the inner member is no more than about 1.8 mm.

In some embodiments, the overall length of the catheter shaft is no more than about 50 cm. In some embodiments, an outer diameter of the catheter shaft immediately proximal to a proximal attachment of the balloon to the shaft is no greater than about 2 mm. Also in some embodiments, an outer diameter of the balloon when fully inflated is at least 3 mm, and a working length of the balloon is at least 10 mm. In some embodiments, the balloon can withstand inflation pressures of up to about 12 atmospheres. The balloon may include, in some embodiments, a working length of between about 10 mm and about 60 mm, an outer diameter of between about 3 mm and about 24 mm, a proximal tapered portion extending from a proximal end of the working length to a proximal attachment point with the catheter shaft and having a length of between about 1 mm and about 6 mm, and a distal tapered portion extending from a distal end of the working length to a distal attachment point with the catheter shaft and having a length of between about 1 mm and about 6 mm. In some embodiments, the balloon may have an outer surface that is slip-resistant.

Regarding the stylet, in some embodiments it can extend out of the distal end of the catheter shaft a length of about 1 mm to about 5 cm. In some embodiments, the stylet may include a core wire tapered from the proximal end to the distal end of the stylet and a coil disposed over at least a distal portion of the core wire. In some embodiments, the stylet may be malleable. In some embodiments, the flexible portion of the stylet may include a bend relative to a longitudinal axis of the stylet of up to about 20 degrees, where the bend causes the distal portion of the balloon catheter to bend when the stylet is disposed therein. In some embodiments, the stylet may include a locking member coupled with its proximal end for locking the stylet within a hub coupled with the catheter shaft such that rotating the catheter shaft causes the stylet to rotate. Optionally, the stylet may include a light emitting portion at or near its distal end, and wherein a proximal end of the stylet is removably couplable with a light source.

In some embodiments, the system may include an endoscope for viewing the balloon catheter during use. Optionally, the endoscope may be removably couplable with the balloon catheter in some embodiments.

In another aspect, a kit for dilating a stenotic region in an airway of a patient may include: a catheter shaft having a proximal portion, a distal portion, a stylet lumen, an inflation lumen and an overall length of less than 70 cm; an inflatable balloon disposed along the distal portion of the catheter shaft and in fluid communication with the inflation lumen; a stylet; and user instructions. The stylet may have a proximal portion, a distal portion, and a length sufficient to allow the stylet to extend beyond a distal end of the catheter shaft when the stylet is housed within the stylet lumen, where the stylet proximal portion is less flexible than the stylet distal portion and the stylet distal portion is bendable and able to retain a bent configuration when disposed within the stylet lumen. The user instructions may be for: advancing the balloon catheter with the stylet disposed therein through the airway to position the inflatable balloon at the stenotic region; maintaining a position of the catheter relative to the patient to maintain the position of the balloon within the stenotic region by holding the proximal portion of the balloon catheter; and inflating the balloon of the catheter with the stylet in the catheter to dilate the stenotic region of the airway.

Additional elements and embodiments are described further below.

BRIEF DESCRIPTION OF THE DRAWINGS

FIG. 6A is a side view of an airway balloon catheter;

FIG. 6B is a magnified view of section AD from FIG. 6A;

FIG. 8A is a side view of a bump tubing used to form an outer member of an airway balloon catheter shaft;

FIGS. 8B and 8C are cross-sectional views of the bump tubing of FIG. 8A at sections C-C and F-F, respectively;

FIG. 9A is a side view of a bump tubing used to form an inner member of an airway balloon catheter shaft;

FIGS. 9B and 9C are cross-sectional views of the bump tubing of FIG. 8A at sections C-C and K-K, respectively;

DETAILED DESCRIPTION

Before the present devices and methods are described, it is to be understood that this disclosure is not limited to particular embodiments described, as such may, of course, vary. It is also to be understood that the terminology used herein is for the purpose of describing particular embodiments only, and is not intended to be limiting.

Figure 1:
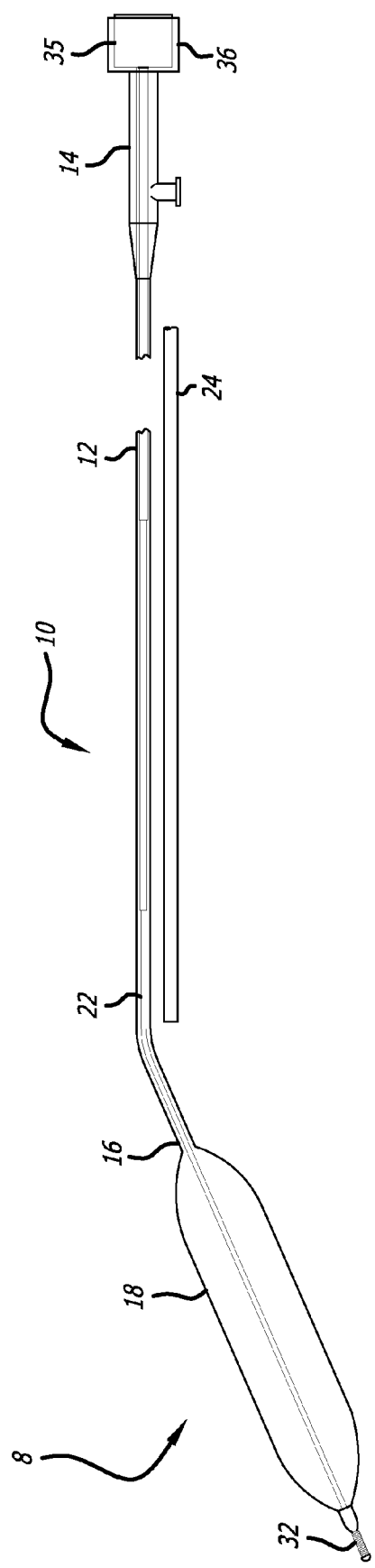
FIG. 1 is a planar view of a system for dilating a stenosis in the airway of a patient, including a balloon catheter, a stylet, and an optional endoscope.

Referring to FIG. 1, one embodiment is directed to a system 8 for dilating a stenosis in the airway of a patient. In this embodiment, the system 8 includes a balloon catheter 10 and a stylet 22. Optionally, the system may also include an endoscope 24, such as a bronchoscope or the like. As will be described further below, use of a balloon catheter 10 and stylet 22 together, each having dimensions, stiffness characteristics, and other features specifically configured for dilation of an airway, may help facilitate airway dilation procedures and combat various shortcomings of the prior art, such as difficulty advancing a dilator into a constricted passage and/or watermelon seeding of the balloon out of the stricture.

In the pictured embodiment, the balloon catheter includes a catheter shaft 12 (or "elongate tubular element") with a proximal section 14 and a distal section 16 and an inflatable balloon 18 disposed on the distal section 16. The inflatable balloon 16 is in communication with an inflation lumen. A stylet 22 is also disposed within the catheter shaft 12. In some embodiments, at least a portion of the stylet 22 may have a greater stiffness than at least a portion of the catheter shaft 12, so that when the stylet 22 is bent and inserted within the catheter shaft 12, the catheter shaft 12 at least partially conforms to the shape of the stylet 22. The stylet 22 is used to advance the balloon catheter 10 within an airway of a patient. In this embodiment, the system also includes an endoscope 24 disposed adjacent to the balloon catheter 10 for visualizing the placement of the balloon catheter 10 in the airway of the patient. In use, the balloon catheter 10 is inserted in the airway of the patient and the inflatable balloon 18 is inflated to dilate the stenosis in the airway of the patient.

With reference now to FIGS. 2A, 2B and 10A through 10C, the stylet 22 is described in further detail. In general, and in most embodiments, the stylet 22 includes a stiff proximal portion providing stiffness to the catheter 10 and enabling the catheter 10 to be advanced through a patient's nostril or mouth and into position within a stenotic region of the airway, and a flexible distal portion, which may take a bend and which retains a bent shape when disposed within the balloon catheter 10. In one embodiment, the bend is pre-formed in the stylet. In another embodiment, the flexible portion is malleable, and the user can form the bend. In another embodiment, the bend may be pre-formed and it may also be malleable so the user can change the bend. In some embodiments, the stylet 22 is made of stainless steel, and this material helps the stylet 22 retain its bent shape even when disposed in the catheter 10. This is a significant advantage, since it allows a user to steer the catheter, using the bend.

Referring again to FIGS. 2A, 2B and 10A through 10C, in one embodiment, the stylet 22 may include a core member 26 with a proximal section 28 and a distal section 30, a coil 32 disposed around at least part of the distal section 30 of the core member 26, and a luer lock member 35 coupled with a proximal end of the core member 26 for coupling with a hub on the balloon catheter 10. In alternative embodiments, the stylet 22 may not include a coil. In one embodiment, the core member 26 and/or the coil 32 may be formed of nitinol. In another embodiment, the core member 26 and/or the coil 32 may be formed of stainless steel or other biocompatible material. In an embodiment in which stainless steel is used to form at least the core member 26, the stylet 22 may be advantageously more able to maintain a bent shape when disposed with the balloon catheter 10. The distal portion 30 of the stylet may include a bend or curve 34 that is stiff enough to bend the balloon catheter 10 during the placement of the balloon catheter 10 within the airway of the patient. In another embodiment, the stylet 22 may be provided in a generally straight configuration, as in FIG. 2B. In some embodiments, the stylet 22 may be pre-formed to have a bend 34. In some embodiments, the stylet 22 may alternatively or additionally be malleable, such that a user may bend the stylet 22 and the stylet 22 maintains the user-created bend. In one embodiment, a proximal section 28 of the stylet 22 may be generally stiff, a distal section 30 may be generally malleable, and an extreme distal portion may be atraumatic and very flexible or even floppy. In some embodiments, this variation in flexibility along the length of the stylet 22 may be achieved by using different materials, such as stainless steel and nitinol. In another embodiment, one material such as stainless steel may be used and the diameter of the stylet 22 may be altered to achieve the variation in flexibility along the length of the stylet 22.

According to various embodiments, the stylet 22, core member 26 and coil 32 may have any number of configurations and combinations of dimensions. As shown in FIG. 10C, for example, in one embodiment, core member 26 may include a proximal portion 28 and a distal portion 30 having multiple portions 30a, 30b, 30c, 30d having differing diameters. In various embodiments, any of a number of different diameters, lengths, and the like may be used in forming core member 26. In the embodiment shown, for example, the diameter of the proximal portion is about 0.8 mm the diameter of the first distal portion 30a tapers from about 0.8 mm to about 0.4 mm, the diameter of the second distal portion 30b is about 0.4 mm, the diameter of the third distal portion 30c tapers from about 0.4 mm to about 0.13 mm, and the diameter of the fourth, distal-most distal portion 30d is about 0.13 mm. In one embodiment, the length of the first distal portion 30a is about 6-8 cm, the length of the second distal portion 30b is about 2-4 cm, the length of the third distal portion 30c is about 4-5 cm, and the length of the fourth distal portion is about 3-5 cm. In one embodiment, the core member 26 may be ground down to form the various distal portions 30a-d. For example, in one embodiment, the distal-most fourth distal portion 30d may be ground to a flat configuration having a height of about 0.06 mm, a width of about 0.13 mm, and a length of about 2.5-4.0 cm and preferably about 3.0-3.5 cm. Of course, this is merely one exemplary embodiment, and in alternative embodiments many different dimensions and combinations may be used. Generally, it may be advantageous to provide a core member 26 that tapers over its length so that it can retain a bent configuration along a portion of its length while disposed in a balloon catheter 10 while at the same time providing sufficient proximal stiffness to facilitate pushing the coupled stylet 22 and catheter 10 and also having a flexible, atraumatic distal tip.

Figure 10A:
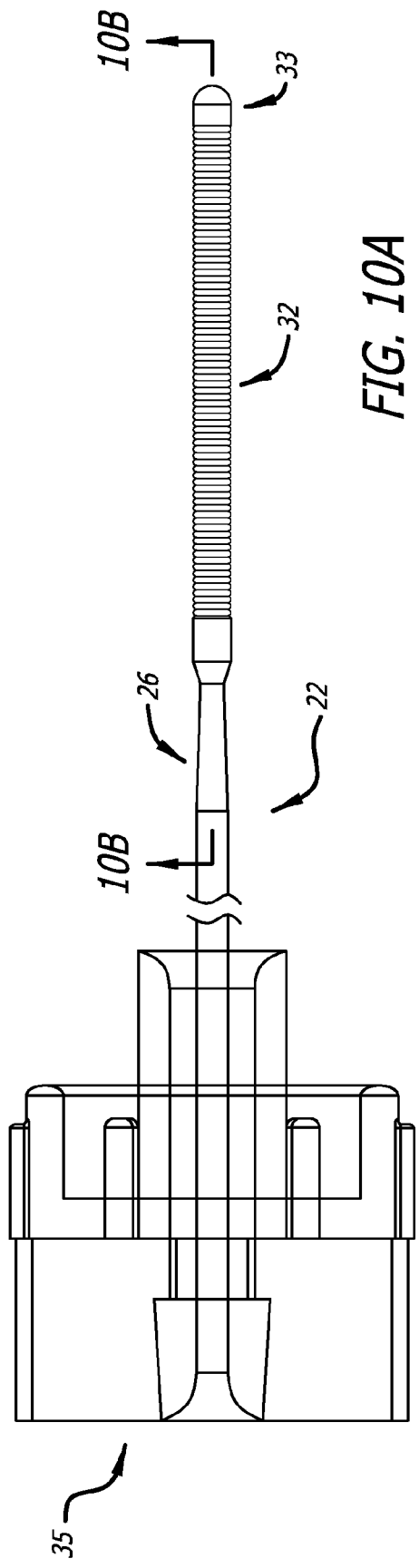
FIGS. 10A and 10B are side views of a stylet with a proximal luer and a distal portion of the stylet, respectively.
Figure 10B:
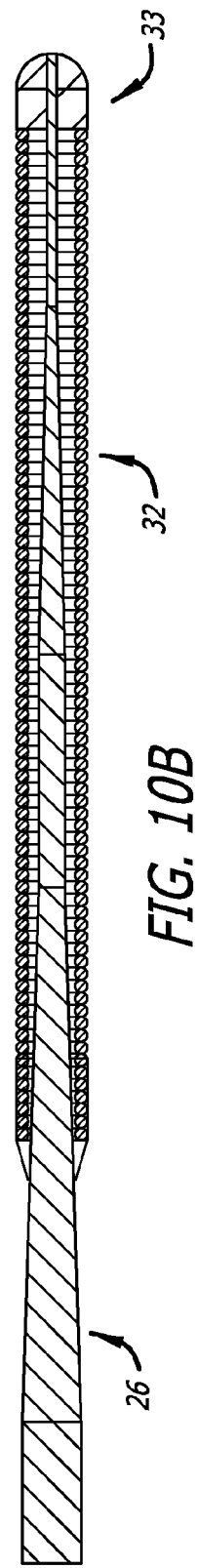
Figure 10C:
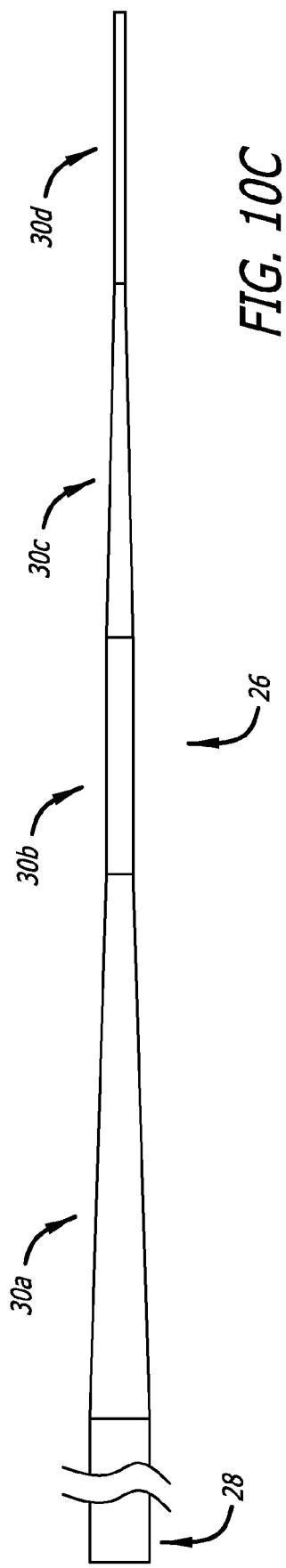
FIG. 10C is a side view of a core member of the stylet of FIGS. 10A and 10B.

Referring to FIGS. 10A and 10B, the coil 34 of the stylet 22 may have any suitable overall length and any of a number of different coil spacings (or "pitches"). For example, where a more flexible distal end of the stylet 22 is desired, a larger pitch (more spacing between coils) may be used. Where a stiffer distal end is desired, a smaller pitch may be used. In one embodiment, for example, the coil 34 may have a pitch of between about 0.13 mm and about 0.25 mm and more preferably about 0.20 mm. The coil 34 may be disposed over any suitable length of the core member 26. At the extremes, the coil 34 may be disposed over the entire length of the core member 26, or the coil 34 may be eliminated from the stylet 22 altogether. In various other embodiments, the coil 34 may be disposed over a length of the core member 26 between about 5 cm and about 25 cm, and more preferably between about 10 cm and about 15 cm. In some embodiments, the coil 32 may be soldered at its proximal and distal ends to the core member 26. In some embodiments, the solder at the distal end may form a solder tip 33. In other embodiments, a separate distal tip member may be added to the stylet 22 via adhesive or other attachment means.

In various embodiments, the stylet 22 may have an overall length approximately as long or slightly longer than the catheter shaft 12 of the balloon catheter 10. In some embodiments, for example, the stylet 22 may include an atraumatic, flexible distal tip portion that extends distally out of the catheter shaft 12 when the stylet 22 is fully disposed within the catheter 10. This tip portion may be, for example, about 0.25 cm to about 8 cm or more preferably about 1-5 cm in length and may facilitate the ability of a user to advance the system 8 through a patient's airway atraumatically. In some embodiments, the overall length of the stylet may vary from about 30 cm to about 80 cm, and more preferably from about 45 cm to about 60 cm. Of the overall length, a flexible distal portion of the stylet 22 may be from about 5-20 cm, and preferably from about 10-15 cm, in some embodiments. The stylet 22 may include a bend 34 having any suitable angle, such as from greater than 0 degrees to about 20 degrees. In one embodiment, the largest diameter of stylet 22 may be about 1.3 mm, and preferably 0.9 mm or less, and the diameter may decrease distally to about 0.13 mm+/−0.013 mm.

Figure 2:
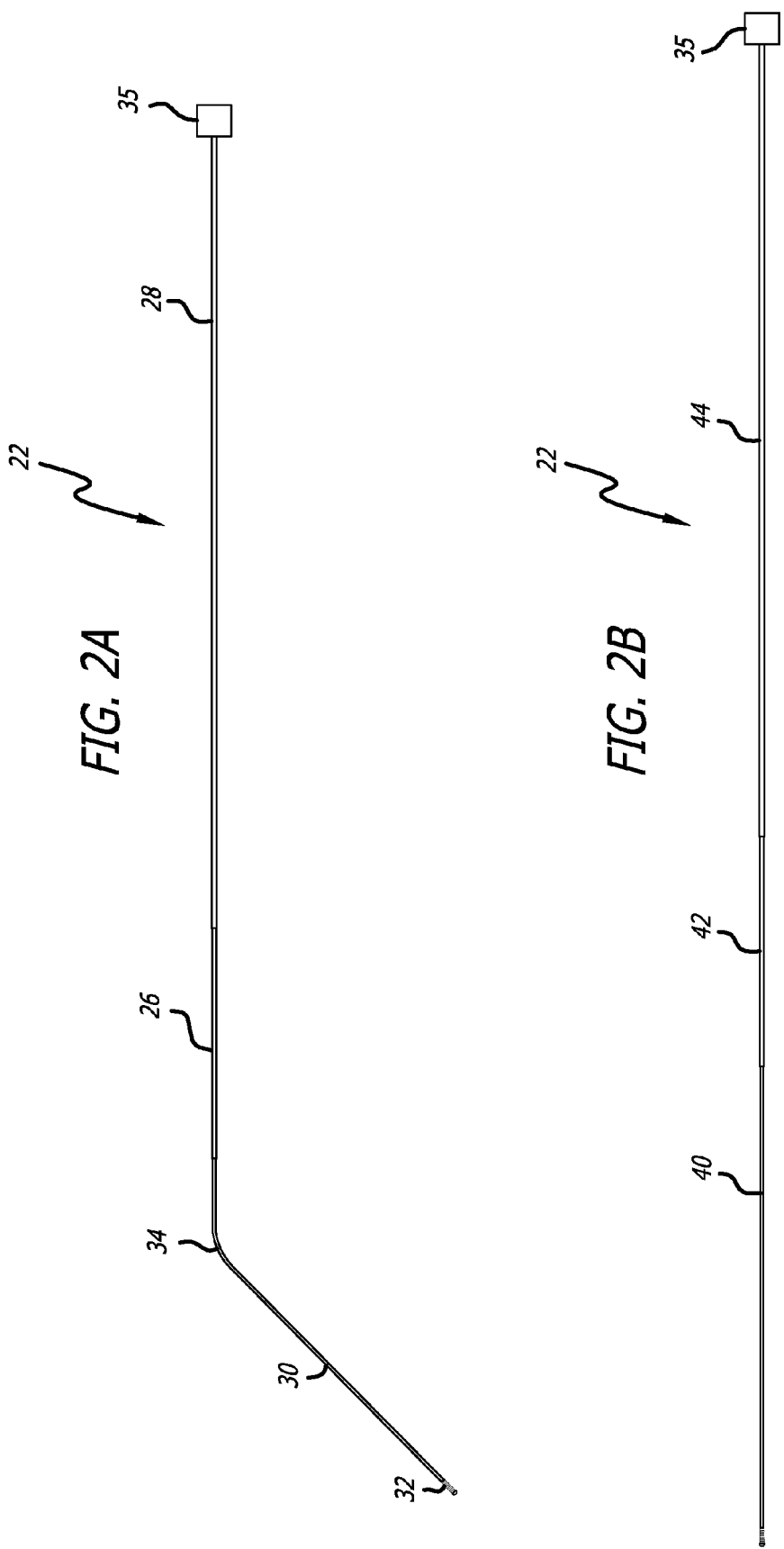
FIG. 2A is a planar view of a stylet having a bend in a distal portion of the stylet.
FIG. 2B is a planar view of a stylet having a generally straight configuration.

In some embodiments, either where the stylet 22 includes a preformed bend 34 or where it is provided in a straight configuration, the stylet 22 may be malleable so that a user can form the bend 34 or change the angle of the bend 34. This malleability allows a user to adjust a bend angle according to the airway anatomy of a particular patient. In most embodiments, the stylet 22 retains the bend 34, or approximately the same bend 34 although it may straighten somewhat, when the bent stylet is placed in the balloon catheter 10. In some embodiments, the bend 34 may be maintained during and sometimes after the balloon catheter 10 is positioned in the airway of a patient. In other embodiments, the stylet 22 may have a stiffness such that the bend 34 partially or completely straightens out in the narrow airway of the patient. As shown in FIG. 2B, one embodiment of the stylet 22 includes three sections, a flexible section 40 near the distal end that can range from about 0.25 cm to about 8 cm or more preferably about 1-5 cm in length. In one embodiment, the flexible section 40 is atraumatic and may or may not include the coil 32. A central section 42 of the stylet may be malleable for introducing a curve or bend to the stylet 22 to help advance and place the balloon catheter 10 within the airway of the patient. The central section 42 may be about 0.5 cm to about 10.0 cm in length in one embodiment. In one embodiment, the malleable central section 42 takes a preformed shape in free space, such as a bend or curve, and then conforms to the shape of the patient's airway. A stiff section 44 is near the proximal end of the stylet 22 and can have a length of about 10 cm to about 35 cm in one embodiment. In one embodiment, any of these three sections 40, 42 or 44 may be bonded to one another. In another embodiment, core member 26 may be ground down in sections to give those sections smaller diameters.

The stylet 22 in one embodiment may have a greater stiffness along a portion of its length where the bend 34 is located or may be formed than the corresponding portion of the balloon catheter 10 that resides over the bend 34. In this embodiment, the catheter shaft 12 conforms to the shape of the stylet 22 (bent or straight) during placement within the stenotic region.

In one embodiment of the system 8, the stylet 22 may be attached to the balloon catheter 10, and in another embodiment, the stylet may be removably connected to the balloon catheter 10. In some embodiments, the stylet 22 may include a luer lock member 35 with threads on the proximal section 28 that screw into opposing threads disposed on a luer 36 of the balloon catheter 10. In another embodiment, the balloon catheter 10 may include a locking mechanism (not shown) to lock the stylet 22 in position within the catheter shaft 12. The locking mechanism can be any mechanical device, include a lever, a ball and pin, and luer. In one embodiment, when the stylet 22 is connected to the balloon catheter 10, the all or part of the distal section 30 of the stylet 22 may extend out of the distal end of the catheter shaft 12. Still in other embodiments, the stylet 22 may be locked to the balloon catheter 10 at different positions or lengths so the distal end of the stylet 22 extends out of or is positioned within the balloon catheter 10 at different lengths. The length, diameter(s) and stiffness characteristics of the stylet 22 may be varied in different embodiments to confer different performance characteristics to the overall system 8.

Use of the stylet 22 while inserting the balloon catheter 10 helps to guide the distal end of the balloon catheter 10 through the airway of the patient and to the stenotic region. The stylet provides increased steerability during advancement of the balloon catheter 10. Torquability of the balloon catheter 10 is also increased when using the stylet 22. In some embodiments, the luer lock member 35 of the stylet 22 and the luer 36 of the balloon catheter 10 mate together, so that the stylet 22 and balloon catheter 10 may be rotated together and thus steered into a constricted portion of an airway.

In one embodiment, the stylet 22 may have a light emitting portion, such as a light emitting distal end or tip. In one such embodiment, for example, the stylet 22 may include one or more light fibers to transmit light from a light source attached to the proximal end of the stylet 22 to its distal end. Light from a light emitting stylet 22 may be used to help a user visualize a patient's airway from the inside using a scope and/or in some cases from the outside via transillumination through the patient's skin. One embodiment of a light emitting guidewire device that may be used or modified to achieve such an illuminating stylet 22 is the Relieva Luma™ Sinus Illumination Guidewire/System, manufactured by Acclarent, Inc. of Menlo Park, Calif. Such an illuminating stylet 22 may have any of the features described above with the additional feature of light emitting capability.

With reference now to FIGS. 6A and 6B, in one embodiment, a balloon catheter 50 may include a catheter shaft 52 having an outer shaft member 54 and an inner shaft member 56, an inflatable balloon 58 attached to the shaft 52 at a proximal attachment point 62 and a distal attachment point 64, and a hub 60 having a stylet port 66 and an inflation port 68. In this embodiment, the outer shaft member 54 is disposed over a portion of the inner shaft member 56, with the latter continuing to the distal end of the catheter 50. The balloon 58 is attached at the proximal attachment point 62 to the outer member 54 and at the distal attachment point 64 to the inner shaft member 56, either via adhesive or other attachment means. Thus, an inflation lumen (too small to view on FIG. 6A) is formed between the inner and outer shaft members 56, 54, with inflation fluid passing into the catheter 50 from an inflation device (not shown), through the inflation port 68, into the inflation lumen, and into the balloon 58. The stylet 22, which is not pictured in FIGS. 6A and 6B, generally resides within an inner lumen of the inner shaft member 56, and may extend distally out of the distal end of the catheter 50 and couple proximally with the hub 60.

In various embodiments, the balloon catheter 50 and its various components may have any number of suitable sizes, shapes and configurations. For example, the balloon 58 may have different lengths and diameters in different embodiments, to accommodate different patient anatomies. The overall catheter length and diameter may also vary. Thus, the following description of embodiments is exemplary only and not limiting of the invention which is defined by the granted claim(s) and equivalents thereof. In some embodiments, for example, the overall length of the balloon catheter 50 (i.e., from the proximal end of the hub 60 to the distal end of the catheter shaft 52) is about 35-70 cm, more preferably less than or equal to about 50 cm, and more preferably about 45 cm±5 cm. Limiting the overall length of the catheter 50 to these ranges makes the catheter easier to handle and manipulate with one hand, especially compared to the currently available vascular catheters, which are much longer and floppier than the present catheter 50 and thus more challenging to use for an airway dilation procedure.

The working length of the balloon 58 in FIGS. 6A and 6B is about 40 mm±2 mm. By "working length" it is meant the length between the two tapered portions of the balloon 58. In alternative embodiments, the working length of the balloon 58 may range from between about 10 mm and about 60 mm and more preferably about 16-45 mm. In one embodiment, a variety of lengths may be provided, including about 16 mm, 24 mm and 40 mm. The outer diameter of the fully inflated working length of the balloon 58 may also vary. In the embodiment shown in FIGS. 6A and 6B, the balloon 58 has an inflated diameter of about 14.1 mm±0.5 mm. In some embodiments, the balloon diameter may range from about 3 mm to about 24 mm and more preferably about 5-15 mm. In one embodiment, a variety of diameters may be provided, including about 5 mm, about 7 mm, about 10 mm, about 14 mm, about 20 mm and about 24 mm. For example, a combination of balloon sizes and lengths may be provided, such that a physician may choose an appropriate size for an adult or pediatric patient. In one example, the following combinations may be provided (first dimension is diameter, second is length): 5 mm×24 mm; 7 mm×24 mm; 10 mm×40 mm; and 14 mm×40 mm. Of course, any of a number of other combinations of sizes of balloons 58 may be provided.

In various embodiments, any suitable material may be used to form the balloon 58. The balloon 58 may be compliant, semi-compliant or non-compliant, according to various embodiments, although in a preferred embodiment the balloon 58 is either semi-compliant or non-compliant. The balloon 58 may be made of nylon or other polymer or the like, such as in one example PTFE. In some embodiments, the balloon 58 may include an outer slip-resistant surface, which may be formed by a textured surface or a coating. Such a surface may help prevent watermelon seeding of the balloon 58 out of an airway stricture during inflation and/or may facilitate re-wrapping the balloon 58 by hand after deflation, for example if the balloon 58 is to be used for a second or subsequent dilation procedure.

In some embodiments, the inflatable balloon 58 may inflate preferentially. For example, the inflatable balloon 58 can be designed to inflate in a dumbbell shape. Typically, this shape can be created by making the proximal and distal ends of the balloon 58 with a different balloon wall thickness than the wall thickness of the central portion of the balloon 58. In other embodiments, a sleeve may be placed around the central portion of the balloon 58 to prevent the central section from inflating at the same rate as the proximal and distal ends of the balloon 58. Also, the central section of the balloon 58 may be heat treated to prevent it from inflating at the same rate as the ends of the balloon 58. Still in other embodiments, sections of the balloon 58 may inflate at different rates depending on the location of the inflation ports.

According to various embodiments, the catheter shaft 52 (outer shaft member 54 and inner shaft member 56) may be formed of any suitable material. In some embodiments, it may be advantageous to form the shaft 52 from material(s) selected so that the shaft 52 is unlikely to kink when bent, such as when bent by the stylet 22 and/or a user. One such material, for example, is Pebax, although other polymers may be used in alternative embodiments.

The outer shaft member 54, the inner shaft member 56, or both may also have any suitable color and may include one or more shaft markings. The shaft color and markings may be built into the shaft 52 by using a colored material or may be added by applying paint or another colorant. In one embodiment, the shaft 54 may have a dark color, such as black or dark blue, and one or more light colored markings may be applied over the dark shaft 54. In various embodiments, the markings (not shown in the figures) may include direct visualization markings (viewed directly with the naked eye or an endoscope), radiographic markings (viewed with a radiographic device such as intraoperative fluoroscopy), or both. For example, in one embodiment, two radiographic markings may be positioned in the inner shaft member 56 at the locations of the two working ends of the balloon 58, and two direct visualization markings may be positioned on the outer shaft 54 approximately 1 cm and 2 cm proximal to the proximal attachment point. Optionally, additional direct visualization markings may be included. The direct visualization markings may be viewed with a bronchoscope or other endoscope to help a physician approximate the location of the balloon 58 relative to anatomy, while the radiographic markings may be viewed with a fluoroscopy device to see where the working ends of the balloon 58 are located relative to an airway constriction. In various embodiments, any suitable combination, size and color of markings may be used. One example of shaft color and shaft markings, which could be used or modified for the balloon catheter 50, is the Relieva Solo Pro™ Sinus Balloon Catheter, manufactured by Acclarent, Inc. of Menlo Park, Calif.

Referring now to FIGS. 8A-8C, in one embodiment the outer shaft member 54 of the catheter shaft 52 may include a distal portion 70 (FIG. 8C) having a first diameter and a proximal portion 72 (FIG. 8B) having a second, larger diameter. In one embodiment, this difference in diameter may be achieved by using "bump tubing," which has a larger wall thickness proximally than distally. Alternatively, the difference could be built into the outer shaft member 54 by an extrusion or other technique. In one embodiment, for example, the outer diameter of the proximal portion 72 may be about 2.1 mm, and the outer diameter of the distal portion 70 may be about 1.8 mm, with the inner diameter of both being about 1.6 mm. In some embodiments, the maximum outer diameter of the outer shaft member 54 immediately proximal to its attachment to the balloon 58 may be about 1.5-2.5 mm and in one embodiment about 2 mm (or about 1.8 mm). Limiting the outer diameter of outer shaft 54 near the balloon 58 within this range enables or at least enhances the ability of a user to view the balloon 58 using an endoscope in the airway. A larger outer shaft diameter makes such visualization difficult or impossible, because there is not sufficient room in the airway to fit the catheter shaft 52 and the endoscope 24. The inner diameter of outer member may be about 1.3 mm-1.8 mm, more preferably about 1.5 mm-1.65 mm, and in one embodiment about 1.6 mm-1.62 mm.

Referring now to FIGS. 9A-9C, the inner shaft member 56 of the catheter shaft 52 may also include a distal portion 74 (FIG. 9C) having a first diameter and a proximal portion 76 (FIG. 9B) having a second, larger diameter. In one embodiment, for example, the proximal portion 76 may have an outer diameter of about 1.5 mm±0.025 mm, and the distal portion 74 may have an outer diameter of about 1.2 mm±0.025 mm. In some embodiments, the inner and outer diameters of the inner shaft member 56 may be no more than about 1.3 mm and 1.8 mm respectively, more preferably no more than and 1.02 mm and 1.3 mm respectively, and in one embodiment no more than about 0.97 mm and 1.22 mm respectively. Again, bump tubing may be used in one embodiment.

Referring again to FIGS. 6A and 6B, in some embodiments, the inner shaft member 56 may extend distally beyond the distal end of the balloon 58 by about 1 mm to about 10 mm, more preferably by about 5 mm±1 mm. This distal end of the inner shaft member 56 may act as an atraumatic tip, along with a protruding distal end of the stylet 22, which may extend further out of the inner shaft member. In some embodiments, where a larger diameter balloon is used (10 mm or more, for example), a small segment of the inner shaft member 56 toward its distal end may have a larger outer diameter, so that the larger diameter balloon may be adequately bonded to the inner shaft member 56 at the distal attachment point 64. This serves the purpose of keeping the inner shaft member 56 small along the rest of its length (i.e., lower profile means it is easier to advance through the airway), while still allowing the larger balloon to be bonded to it. In one embodiment, the larger outer diameter may be performed by adding material to the inner shaft member 56 at the distal attachment point 64 before bonding. In another embodiment, bump tubing may be used, with the inner shaft member 56 constructed with the larger diameter built-in at the distal attachment point 64.

The inner and outer diameters of the inner shaft member 56 and outer shaft member 54 may confer several advantages to the balloon catheter 50. For example, moving from a larger diameter proximally to a smaller diameter distally while keeping the inner diameter of the shaft 52 as large as possible, helps minimize deflation time of the balloon 58 after an inflation. This allows for quick removal and/or adjustment of the balloon 58 after a dilation. This quick deflation can be achieved while also providing a relatively small diameter catheter shaft 52 toward the balloon 58 and the distal end of the catheter 50. This facilitates both advancement of the catheter 50 into a desired treatment position in the airway as well as viewing the proximal end of the balloon 58 with a bronchoscope positioned in the airway. The small profile catheter shaft 52, combined with a balloon 58 having a sufficiently large diameter to dilate an airway constriction, allows a physician to treat both pediatric and adult patients who have very different anatomies.

Figure 7A:
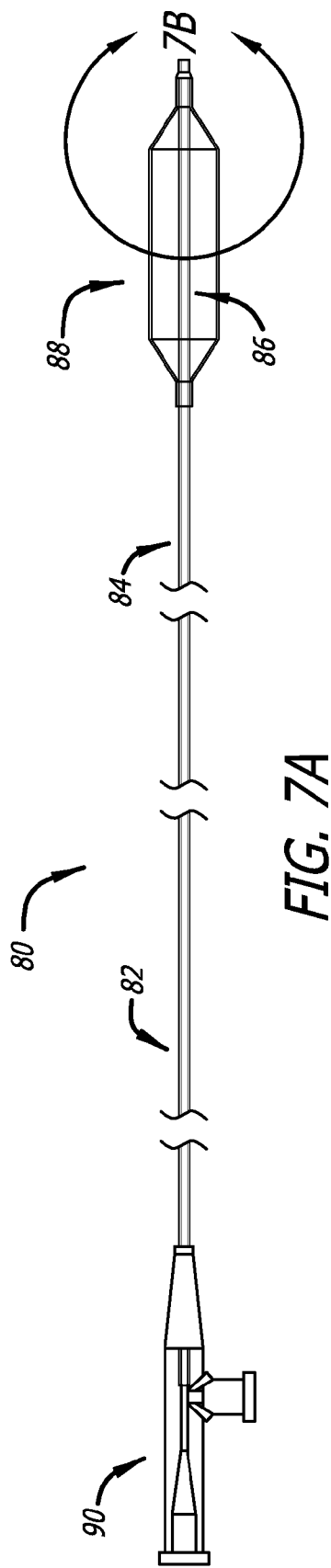
FIG. 7A is a side view of an airway balloon catheter.
Figure 7B:
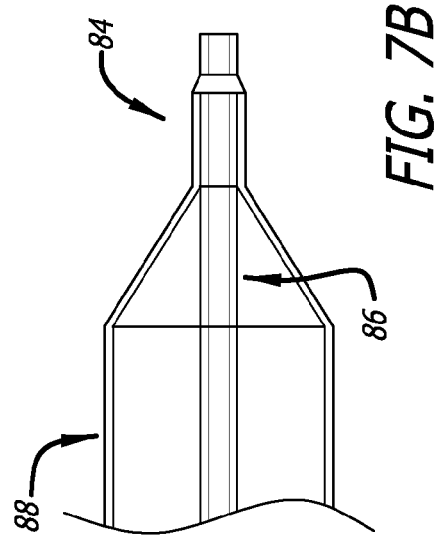
FIG. 7B is a magnified view of section AC from FIG. 7A.

Referring now to FIGS. 7A and 7B, another embodiment of a balloon catheter 80 may include a catheter shaft 82 having an inner shaft member 86 and an outer shaft member 84, a balloon 88 coupled with the shaft 82 at or near its distal end, and a hub 90 coupled with the shaft 82 at or near its proximal end. This embodiment of the balloon catheter 80 is similar to the balloon catheter 50 of FIGS. 6A and 6B but has a differently sized balloon 88. In this embodiment, the balloon 88 is about 22-26 mm long and about 4.5-5.5 mm in diameter when fully inflated. As mentioned previously, in various embodiments any of a number of differently sized balloons may be provided. Physicians may be provided with the choice of balloon sizes to address pediatric patients or adult patients having differently sized airways. In embodiments such as that shown in FIGS. 7A and 7B, with a smaller diameter balloon 88 than the earlier describe balloon catheter 50, the inner shaft member 86 may not increase in diameter at the location of the distal attachment point (FIG. 7B). The increased diameter described earlier to accommodate a larger diameter balloon 58 may not be necessary with a smaller diameter balloon 88. Generally, any features described above may be included in this embodiment of the balloon catheter 80.

In some embodiments, the distal end of the catheter shaft 84 may be sealed to prevent the stylet 22 from extending out of the distal end. The balloon catheter 80 is compatible with a bronchoscope 24, endoscope or other scope device for direct visualization of the stenotic region. Further, the balloon catheter 80 can be integrated with an illuminating guidewire (for example, the Relieva Luma™ Sinus Illumination Guidewire from Acclarent, Inc.). The illuminating guidewire device is connected to a light source and includes an illuminating portion at a distal end that illuminates. Illumination of the illuminating guidewire device can provide additional light in the airway of the patient to visualize the placement of the balloon catheter at the stenotic region.

Figure 3:
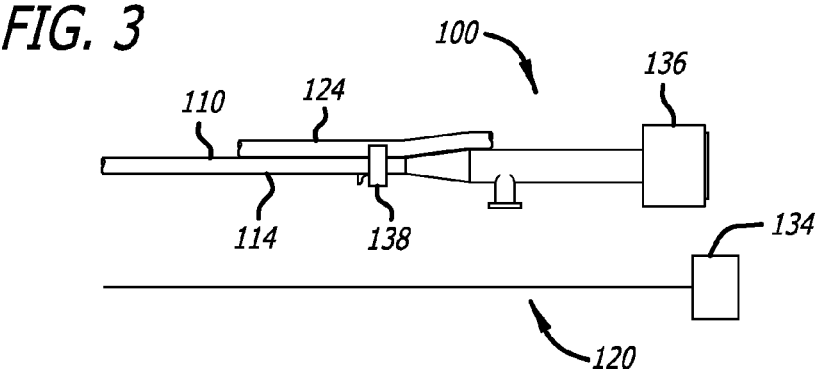
FIG. 3 is a partial perspective view of a grip disposed on an elongated tubular member of a balloon catheter that is holding an endoscope.

Referring to FIG. 3, in one embodiment, an airway dilation balloon catheter system 100 may include a balloon catheter 110, a stylet 120, a scope 124, and a coupling member 138 for coupling the scope 124 to the balloon catheter 110. The balloon catheter 110 may include a shaft 114 and a luer 136, which locks with a luer lock member 134 of the stylet 120. In one embodiment, the coupling member 138 may allow the scope 124 to be removably coupled with the catheter 110. In one embodiment, the scope 124 may be frictionally fit into the coupling member 138. In some embodiments, the coupling member 138 may comprise a handle. As shown in FIG. 3, the scope 124 may be secured into the coupling member 138 on either side of the balloon catheter 110. Securing the scope 124 to the balloon catheter 110 helps to prevent slippage during dilation of the inflatable balloon. Also, securing the scope 124 to the balloon catheter 110 allows the physician to hold both devices in a single hand. In another embodiment, the coupling member 138 can be attached to the luer 136 of the balloon catheter 110.

Figure 4:
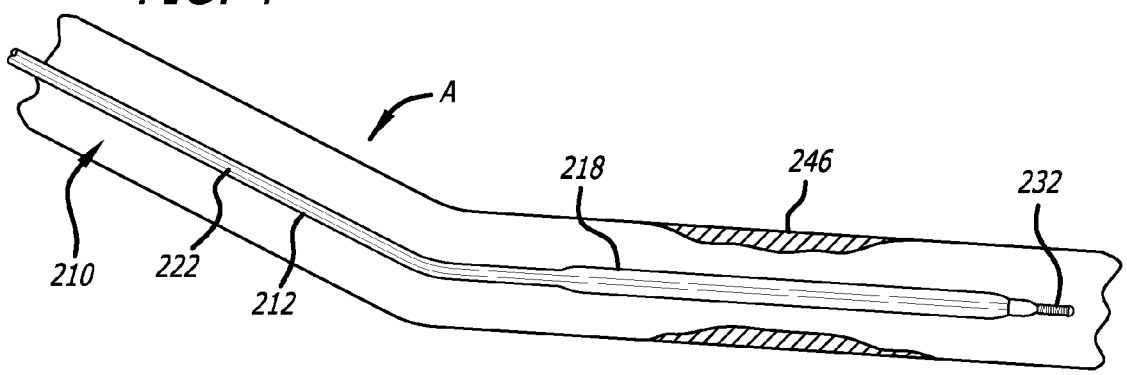
FIG. 4 is a cross-sectional view of a balloon catheter being introduced into the airway of a patient using a stylet with a bent region to bend the balloon catheter during delivery.
Figure 5:
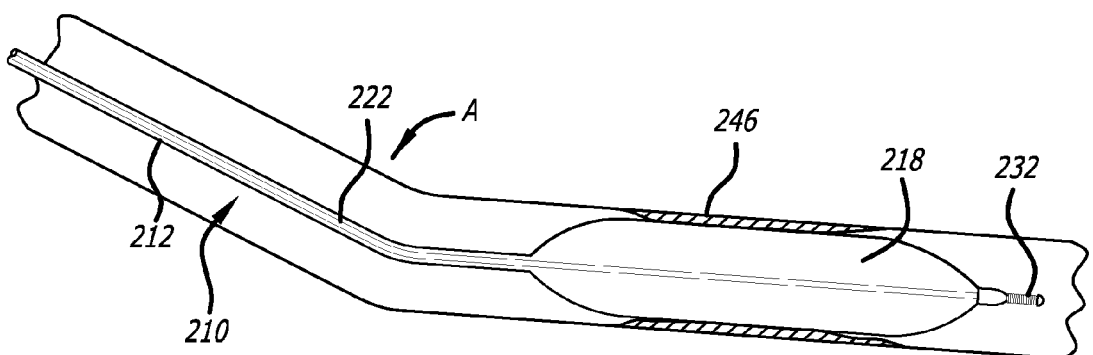
FIG. 5 is the cross-sectional view of the balloon catheter from FIG. 4 positioned at a stenotic region of the airway with the balloon inflated to dilate the stenotic region.

With reference now to FIGS. 4 and 5, a method for dilating an stenotic region 246 in an airway A, such as in a case of subglottic stenosis, is shown. In one embodiment, the method includes introducing an airway dilation system 210 through the mouth and into the airway of the patient. As described in detail above, the airway dilation system 210 may include a balloon catheter 212 with an inflatable balloon 218, disposed over a stylet 222, with a distal tip 232 of the stylet 222 protruding from the catheter 212 and acting as an atraumatic tip. Optionally, in some embodiments the system may include a bronchoscope (not shown) or other scope device. In some embodiments, the method may involve bending the airway dilation system 210, either by the user or by the manufacturer of the system 210. In some cases, the stylet 222 may be bent and then inserted into the balloon catheter 212, while in other cases the stylet 222 and balloon catheter 212 may be bent together, with the stylet 222 already residing in the catheter 212. Thus, in some cases, the stylet 222 may be malleable while in others it may not. The support of the stylet 222 and the bend in the overall system 210 may help a physician navigate the system 210 through the patient's airway to position the balloon 218 within at least a portion of the stenotic region 246. As shown in FIG. 4, the inflatable balloon 218 of the catheter 212 is in an unexpanded configuration during advancement and placement of the balloon catheter 212.

As shown in FIG. 5, once the balloon 218 is positioned within the stenotic region 246 of the airway A, the inflatable balloon 218 is inflated to dilate the stenotic region 246. In some embodiments, the stylet may be formed such that the bent or curved region of the stylet straightens out once the balloon catheter is positioned with the narrow airway A of the patient. In other embodiments, as in FIG. 5, the bend in the system 210 may be retained even when positioned in the airway A.

In one embodiment, the stylet distal tip 232 may include an illumination capability. In such an embodiment, the method may further include illuminating the stylet distal tip 232 and viewing the illumination from inside the airway (using a scope) and/or from outside the patient via transillumination.

In some embodiments, the stylet 222 remains in the balloon catheter 212 during inflation of the balloon 218. Maintaining the stylet 222 in the catheter 212 during inflation may give the catheter 212 added column strength and help maintain the position of the balloon 218 within the stenotic region 246, thus avoiding watermelon seeding. In an alternative embodiment, the method may include removing the stylet 222 from the balloon catheter 212 before inflating. The stylet 222 may be removed from the balloon catheter 212, for example, after the balloon catheter 212 is properly positioned within the airway A of the patient. In another embodiment, the stylet 222 can be removed after the stenosis has been dilated but before removing the balloon catheter 212 from the patient.

The method may also include advancing an endoscope or bronchoscope (not shown) along the airway A of the patient and positioning a distal end of the endoscope near the stenotic region 246 to visualize placement of the airway dilation system 210. The endoscope may be attached to the balloon catheter 212 using the coupling member 138 in one embodiment, to help prevent movement and slippage during balloon dilation. After the dilation is performed, the endoscope can detached from the grip and removed from the patient. Alternatively, the endoscope may be separate from the catheter 212. In alternative embodiments, the endoscope may be positioned alongside the balloon catheter 212 or the endoscope may be positioned within or through the balloon catheter 212. In another embodiment, the method of dilating the subglottic stenosis includes inserting a bronchoscope into the airway A of the patient and then passing the balloon catheter 212 through the bronchoscope.

In one embodiment, the method may include inflating the inflatable balloon 218 more than once to dilate the stenotic region 246 of the airway A. FIG. 5 shows the inflatable balloon in an expanded configuration to dilate the stenotic region. The physician will inflate the inflatable balloon 218 to a desired pressure during each dilation of the stenosis. Proper dilation of the stenotic region can 246 be confirmed by visualizing the region with the bronchoscope/endoscope.

The airway dilation system 210 and method described above increase the ease of use for the physician performing the dilation of the stenotic region 246 in the airway A of the patient. In some embodiments, the physician can manipulate the system 210 using one hand, thus leaving the other hand free to hold a bronchoscope or other device. The combination of the balloon catheter 212, with its advantageous length, shaft and balloon diameters and overall configuration, and the stylet 222, with its bend to facilitate airway navigation, will likely make an airway dilation procedure easier and more often successful. Further, the atraumatic design of the balloon catheter 212 and stylet 222 helps prevent damage to the airway A and vocal cords of the patient during delivery and removal. Also, the design helps prevent movement and slippage of the balloon catheter 212 during dilation of the stenotic region 246, which translates into a more controlled dilation.

The methods and devices described herein make reference to certain examples and embodiments, but various additions, deletions, alterations and modifications may be made to these examples and embodiments and or equivalents may be substituted without departing from the intended spirit and scope of what is disclosed. For example, any element or attribute of one embodiment or example may be incorporated into or used with another embodiment or example, unless to do so would render the embodiment or example unsuitable for its intended use. In addition, many modifications may be made to adapt a particular situation, material, composition of matter, process, process step or steps, to the objective, spirit and scope of the present disclosure. All such modifications are intended to be within the scope of the claims appended hereto.

What is claimed:

1. A system for dilating a stenotic region in an airway of a patient, the system comprising:
   (a) a catheter shaft comprising:
      (i) an outer tube comprising:
         (A) a first proximal portion comprising a first outer diameter,
         (B) a first distal portion comprising a second outer diameter smaller than the first diameter, and
         (C) a first intermediate portion located between the first proximal portion and the first distal portion, wherein the first intermediate portion has a first tapered outer diameter from the first outer diameter to the second outer diameter;
      (ii) an inner tube comprising:
         (A) a second proximal portion comprising a third outer diameter,
         (B) a second distal portion comprising a fourth outer diameter,
         (C) a second intermediate portion located between the second proximal portion and the second distal portion, wherein the second intermediate portion has a second tapered outer diameter from the third outer diameter toward the fourth outer diameter, wherein the fourth outer diameter is larger than a portion of the second tapered outer diameter directly adjacent to the fourth outer diameter,
      wherein the inner tube defines a stylet lumen, wherein the inner tube extends through the outer tube, wherein a space defined between the inner tube and the outer tube forms an inflation lumen, wherein the distal portion of the inner tube extends past the distal portion of the outer tube;
   (b) an inflatable balloon, wherein a proximal end of the balloon is attached to the second outer diameter of the outer tube of the catheter shaft, wherein a distal end of the balloon is attached to the fourth outer diameter of the inner tube of the catheter shaft, wherein the inflatable balloon is in fluid communication with the inflation lumen; and
   (c) a stylet comprising:
      (i) a proximal portion,
      (ii) a distal portion, and
      (iii) a length sufficient to allow the stylet to extend beyond the distal portion of the inner tube when the stylet is housed within the stylet lumen, wherein the proximal portion of the stylet is less flexible than the distal portion of the stylet and the distal portion of the stylet is bendable and able to retain a bent configuration when disposed within the stylet lumen;
   wherein the stylet includes a locking member coupled with its proximal end for locking the stylet within a hub coupled with the catheter shaft such that rotating the catheter shaft causes the stylet to rotate.

2. The system of claim 1, wherein the distal portion of the outer tube and the distal portion of the inner tube are more flexible than the proximal portion of the outer tube and the proximal portion of the inner tube.

3. The system of claim 1, wherein the hub comprises:
   an inflation port in communication with the inflation lumen; and
   a stylet port in communication with the stylet lumen.

4. The system of claim 1, wherein the balloon has an outer diameter of at least 12 mm.

5. The system of claim 1, wherein an inner diameter of the inner member is no more than about 1.2 mm and an outer diameter of the inner member is no more than about 1.8 mm.

6. The system of claim 1, wherein the overall length of the catheter shaft is no more than about 50 cm.

7. The system of claim 1, wherein an outer diameter of the outer tube of the catheter shaft immediately proximal to a proximal attachment of the balloon to the shaft is no greater than about 2 mm.

8. The system of claim 7, wherein an outer diameter of the balloon when fully inflated is at least 3 mm, and wherein a working length of the balloon is at least 10 mm.

9. The system of claim 7, wherein the balloon can withstand inflation pressures of up to about 12 atmospheres.

10. The system of claim 1, wherein the balloon comprises:
    a working length of between about 10 mm and about 60 mm;
    an outer diameter of between about 3 mm and about 24 mm;
    a proximal tapered portion extending from a proximal end of the working length to a proximal attachment point with the catheter shaft and having a length of between about 1 mm and about 6 mm; and
    a distal tapered portion extending from a distal end of the working length to a distal attachment point with the catheter shaft and having a length of between about 1 mm and about 6 mm.

11. The system of claim 1, wherein the balloon has an outer surface that is slip-resistant.

12. The system of claim 1, wherein the stylet can extend out of the distal end of the catheter shaft a length of about 1 mm to about 5 cm.

13. The system of claim 1, wherein the stylet comprises:
    a core wire tapered from the proximal end to the distal end of the stylet; and
    a coil disposed over at least a distal portion of the core wire.

14. The system of claim 1, wherein the stylet is malleable.

15. The system of claim 1, wherein the flexible portion of the stylet includes a bend relative to a longitudinal axis of the stylet of up to about 20 degrees, wherein the bend causes the distal portion of the catheter shaft to bend when the stylet is disposed therein.

16. The system of claim 1, wherein the stylet includes a light emitting portion at or near its distal end, and wherein a proximal end of the stylet is removably couplable with a light source.

17. The system of claim 1, further comprising an endoscope for viewing the balloon catheter during use.

18. The system of claim 1, wherein the hub is stationary.

* * * * *